US008548575B2

(12) United States Patent
Marcovecchio et al.

(10) Patent No.: US 8,548,575 B2
(45) Date of Patent: *Oct. 1, 2013

(54) SYSTEM FOR VERIFYING THE INTEGRITY OF CARDIAC COMPLEX TEMPLATES

(75) Inventors: Alan F. Marcovecchio, Woodbury, MN (US); William Hsu, Ann Arbor, MI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 61 days.

This patent is subject to a terminal disclaimer.

(21) Appl. No.: 13/208,252

(22) Filed: Aug. 11, 2011

(65) Prior Publication Data
US 2011/0295135 A1  Dec. 1, 2011

Related U.S. Application Data

(60) Division of application No. 12/685,281, filed on Jan. 11, 2010, now Pat. No. 8,019,408, which is a continuation of application No. 11/287,631, filed on Nov. 28, 2005, now Pat. No. 7,653,430, which is a division of application No. 09/921,348, filed on Aug. 2, 2001, now Pat. No. 6,996,434, which is a continuation of application No. 09/267,306, filed on Mar. 12, 1999, now Pat. No. 6,312,388.

(51) Int. Cl.
*A61B 5/04* (2006.01)

(52) U.S. Cl.
USPC .......................................... 600/509

(58) Field of Classification Search
USPC .................. 600/508–509, 513, 519
See application file for complete search history.

(56) References Cited

U.S. PATENT DOCUMENTS

| | | | |
|---|---|---|---|
| 4,023,564 A | 5/1977 | Valiquette et al. |
| 4,090,505 A | 5/1978 | Mortara |
| 4,316,249 A | 2/1982 | Gallant et al. |
| 4,323,074 A | 4/1982 | Nelms |
| 4,336,810 A | 6/1982 | Anderson et al. |
| 4,407,288 A | 10/1983 | Langer et al. |

(Continued)

FOREIGN PATENT DOCUMENTS

| | | |
|---|---|---|
| DE | 4405827 | 6/1995 |
| EP | 0469817 A2 | 2/1992 |

(Continued)

OTHER PUBLICATIONS

"U.S. Appl. No. 09/267,306, Communication mailed Jul. 21, 2000", 1 pg.

(Continued)

*Primary Examiner* — Mark W Bockelman
(74) *Attorney, Agent, or Firm* — Schwegman Lundberg & Woessner, P.A.

(57) ABSTRACT

A method and system for verifying the integrity of normal sinus rhythm (NSR) templates and updating the NSR template after selected time intervals. At selected time intervals after establishing a NSR template, cardiac complexes are sensed and values for one or more cardiac parameters are measured. The values of the cardiac parameters are compared to predetermined value ranges for NSR cardiac complexes. When the values of the cardiac parameters fall within the predetermined value ranges, values for the differences between the values of the cardiac parameters for the cardiac complexes and the values for the cardiac parameters of the NSR cardiac complexes are calculated. When the values of the differences are greater than one or more threshold values, the NSR template is updated as a function of the sensed cardiac complexes.

22 Claims, 4 Drawing Sheets

(56) References Cited

U.S. PATENT DOCUMENTS

| | | |
|---|---|---|
| 4,452,248 A | 6/1984 | Keller, Jr. |
| 4,531,527 A | 7/1985 | Reinhold, Jr. et al. |
| 4,583,553 A | 4/1986 | Shah et al. |
| 4,589,420 A | 5/1986 | Adams et al. |
| 4,721,114 A | 1/1988 | DuFault et al. |
| 4,838,278 A | 6/1989 | Wang et al. |
| 4,884,345 A | 12/1989 | Long |
| 4,924,875 A | 5/1990 | Chamoun |
| 5,000,189 A | 3/1991 | Throne et al. |
| 5,010,888 A | 4/1991 | Jadvar et al. |
| 5,014,284 A | 5/1991 | Langer et al. |
| 5,020,540 A | 6/1991 | Cahmoun |
| 5,092,341 A | 3/1992 | Kelen |
| 5,109,842 A | 5/1992 | Adinolfi |
| 5,139,028 A | 8/1992 | Steinhaus et al. |
| 5,156,148 A | 10/1992 | Cohen |
| 5,184,615 A | 2/1993 | Nappholz et al. |
| 5,193,550 A | 3/1993 | Duffin |
| 5,215,098 A | 6/1993 | Steinhaus et al. |
| 5,217,021 A | 6/1993 | Steinhaus et al. |
| 5,240,009 A | 8/1993 | Williams |
| 5,247,021 A | 9/1993 | Fujisawa et al. |
| 5,255,186 A | 10/1993 | Steinhaus et al. |
| 5,269,301 A | 12/1993 | Cohen |
| 5,271,411 A | 12/1993 | Ripley et al. |
| 5,273,049 A | 12/1993 | Steinhaus et al. |
| 5,277,190 A | 1/1994 | Moulton |
| 5,280,792 A | 1/1994 | Leong et al. |
| 5,292,348 A | 3/1994 | Saumarez et al. |
| 5,311,874 A | 5/1994 | Baumann et al. |
| 5,312,445 A | 5/1994 | Nappholz et al. |
| 5,313,953 A | 5/1994 | Yomtov et al. |
| 5,330,504 A | 7/1994 | Somerville et al. |
| 5,331,966 A | 7/1994 | Bennett et al. |
| 5,342,402 A | 8/1994 | Olson et al. |
| 5,350,406 A | 9/1994 | Nitzsche et al. |
| 5,360,436 A | 11/1994 | Alt et al. |
| 5,366,487 A | 11/1994 | Adams et al. |
| 5,388,578 A | 2/1995 | Yomtov et al. |
| 5,400,795 A | 3/1995 | Murphy et al. |
| 5,404,880 A | 4/1995 | Throne |
| 5,411,031 A | 5/1995 | Yomtov |
| 5,421,830 A | 6/1995 | Epstein et al. |
| 5,447,519 A | 9/1995 | Peterson |
| 5,447,524 A | 9/1995 | Alt |
| 5,456,261 A | 10/1995 | Luczyk |
| 5,458,623 A | 10/1995 | Lu et al. |
| 5,478,807 A | 12/1995 | Cronin et al. |
| 5,497,780 A | 3/1996 | Zehender |
| 5,509,927 A | 4/1996 | Epstein et al. |
| 5,520,191 A | 5/1996 | Karlsson et al. |
| 5,542,430 A | 8/1996 | Farrugia et al. |
| 5,549,641 A | 8/1996 | Ayers et al. |
| 5,560,368 A | 10/1996 | Berger |
| 5,560,369 A | 10/1996 | McClure et al. |
| 5,622,178 A | 4/1997 | Gilham |
| 5,634,468 A | 6/1997 | Platt et al. |
| 5,645,070 A | 7/1997 | Turcott |
| 5,676,687 A | 10/1997 | Ayers |
| 5,682,900 A | 11/1997 | Arand et al. |
| 5,683,425 A | 11/1997 | Hauptmann |
| 5,687,737 A | 11/1997 | Branham et al. |
| 5,712,801 A | 1/1998 | Turcott |
| 5,713,367 A | 2/1998 | Arnold et al. |
| 5,724,985 A | 3/1998 | Snell et al. |
| 5,730,142 A | 3/1998 | Sun et al. |
| 5,755,739 A | 5/1998 | Sun et al. |
| 5,759,158 A | 6/1998 | Swanson |
| 5,766,225 A | 6/1998 | Kramm |
| 5,772,604 A | 6/1998 | Langberg et al. |
| 5,778,881 A | 7/1998 | Sun et al. |
| 5,779,645 A | 7/1998 | Olson et al. |
| 5,782,888 A | 7/1998 | Sun et al. |
| 5,792,065 A | 8/1998 | Xue et al. |
| 5,795,303 A | 8/1998 | Swanson et al. |
| 5,797,399 A | 8/1998 | Morris et al. |
| 5,797,849 A | 8/1998 | Vesely et al. |
| 5,817,133 A | 10/1998 | Houben |
| 5,819,007 A | 10/1998 | Elghazzawi |
| 5,819,741 A | 10/1998 | Karlsson et al. |
| 5,848,972 A | 12/1998 | Triedman et al. |
| 5,858,977 A | 1/1999 | Aukerman et al. |
| 6,052,620 A | 4/2000 | Gillberg et al. |
| 6,076,014 A | 6/2000 | Alt |
| 6,096,061 A | 8/2000 | Alt |
| 6,223,078 B1 | 4/2001 | Marcovecchio |
| 6,230,055 B1 | 5/2001 | Sun et al. |
| 6,233,078 B1 | 5/2001 | Harano et al. |
| 6,266,554 B1 | 7/2001 | Hsu et al. |
| 6,275,732 B1 | 8/2001 | Hsu et al. |
| 6,308,095 B1 | 10/2001 | Hsu et al. |
| 6,312,388 B1 | 11/2001 | Marcovecchio et al. |
| 6,314,321 B1 | 11/2001 | Morris |
| 6,353,759 B1 | 3/2002 | Hartley et al. |
| 6,370,431 B1 | 4/2002 | Stoop et al. |
| 6,411,848 B2 | 6/2002 | Kramer et al. |
| 6,430,435 B1 | 8/2002 | Hsu et al. |
| 6,430,438 B1 | 8/2002 | Chen et al. |
| 6,434,417 B1 | 8/2002 | Lovett |
| 6,438,410 B2 | 8/2002 | Hsu et al. |
| 6,442,425 B1 | 8/2002 | Alt |
| 6,449,503 B1 | 9/2002 | Hsu |
| 6,480,734 B1 | 11/2002 | Zhang et al. |
| 6,484,055 B1 | 11/2002 | Marcovecchio |
| 6,684,100 B1 | 1/2004 | Sweeney et al. |
| 6,687,540 B2 | 2/2004 | Marcovecchio |
| 6,708,058 B2 | 3/2004 | Kim et al. |
| 6,728,572 B2 | 4/2004 | Hsu et al. |
| 6,745,068 B2 | 6/2004 | Koyrakh et al. |
| 6,889,081 B2 | 5/2005 | Hsu |
| 6,959,212 B2 | 10/2005 | Hsu et al. |
| 6,978,177 B1 | 12/2005 | Chen et al. |
| 6,996,434 B2 | 2/2006 | Marcovecchio et al. |
| 7,031,764 B2 | 4/2006 | Schwartz et al. |
| 7,039,463 B2 | 5/2006 | Marcovecchio |
| 7,085,599 B2 | 8/2006 | Kim et al. |
| 7,177,685 B2 | 2/2007 | Lincoln et al. |
| 7,184,818 B2 | 2/2007 | Kim et al. |
| 7,203,535 B1 | 4/2007 | Hsu et al. |
| 7,415,307 B2 | 8/2008 | Sharma et al. |
| 7,430,446 B2 | 9/2008 | Li |
| 7,539,536 B2 | 5/2009 | Schwartz et al. |
| 7,653,430 B2 | 1/2010 | Marcovecchio et al. |
| 2002/0032469 A1 | 3/2002 | Marcovecchio |
| 2002/0049474 A1 | 4/2002 | Marcovecchio et al. |
| 2002/0087091 A1 | 7/2002 | Koyrakh et al. |
| 2002/0091333 A1 | 7/2002 | Hsu et al. |
| 2002/0183637 A1 | 12/2002 | Kim et al. |
| 2002/0183639 A1 | 12/2002 | Sweeney et al. |
| 2002/0188215 A1 | 12/2002 | Ferek-Petric |
| 2002/0198461 A1 | 12/2002 | Hsu et al. |
| 2003/0060849 A1 | 3/2003 | Hsu |
| 2003/0074026 A1 | 4/2003 | Thompson et al. |
| 2003/0181818 A1 | 9/2003 | Kim et al. |
| 2004/0093035 A1 | 5/2004 | Schwartz et al. |
| 2004/0116972 A1 | 6/2004 | Marcovecchio |
| 2004/0127806 A1 | 7/2004 | Sweeney |
| 2004/0176694 A1 | 9/2004 | Kim et al. |
| 2004/0243014 A1 | 12/2004 | Lee et al. |
| 2005/0137485 A1 | 6/2005 | Cao et al. |
| 2005/0192506 A1 | 9/2005 | Kim et al. |
| 2005/0256544 A1 | 11/2005 | Thompson |
| 2006/0074331 A1 | 4/2006 | Kim et al. |
| 2006/0079796 A1 | 4/2006 | Marcovecchio et al. |
| 2006/0095083 A1 | 5/2006 | Zhang et al. |
| 2006/0122527 A1 | 6/2006 | Marcovecchio |
| 2006/0155201 A1 | 7/2006 | Schwartz et al. |
| 2006/0161069 A1 | 7/2006 | Li |
| 2006/0281998 A1 | 12/2006 | Li |
| 2007/0142737 A1 | 6/2007 | Cazares et al. |
| 2009/0005826 A1 | 1/2009 | Li |
| 2009/0216289 A1 | 8/2009 | Schwartz et al. |
| 2011/0034817 A1 | 2/2011 | Marcovecchio |

FOREIGN PATENT DOCUMENTS

| | | |
|---|---|---|
| EP | 554208 | 8/1993 |
| EP | 0711531 | 5/1996 |
| EP | 0776631 | 11/1996 |
| EP | 0848965 | 6/1998 |
| WO | WO-9739681 A1 | 10/1997 |
| WO | WO-0047278 A1 | 8/2000 |
| WO | WO-0053089 | 9/2000 |
| WO | WO-0126733 A1 | 4/2001 |

OTHER PUBLICATIONS

"U.S. Appl. No. 09/267,306, Notice of Allowance mailed Apr. 25, 2001", 3 pgs.
"U.S. Appl. No. 09/267,306, Notice of Allowance mailed Aug. 22, 2000", 3 pgs.
"U.S. Appl. No. 09/267,306, Preliminary Amendment filed Mar. 30, 2001", 8 pgs.
"U.S. Appl. No. 09/267,306, Response filed Jan. 12, 2000 to Restriction Requirement mailed May 11, 2000", 3 pgs.
"U.S. Appl. No. 09/267,306, Response filed Aug. 14, 2000 to Communication mailed Jul. 21, 2000", 4 pgs.
"U.S. Appl. No. 09/267,306, Restriction Requirement mailed May 11, 2000", 5 pgs.
"U.S. Appl. No. 09/921,348, Final Office Action mailed Jun. 27, 2005", 4 pgs.
"U.S. Appl. No. 09/921,348, Non-Final Office Action mailed Jan. 26, 2005", 6 pgs.
"U.S. Appl. No. 09/921,348, Notice of Allowance mailed Aug. 10, 2005", 4 pgs.
"U.S. Appl. No. 09/921,348, Notice of Allowance mailed Oct. 4, 2005", 4 pgs.
"U.S. Appl. No. 09/921,348, Preliminary Amendment filed Aug. 2, 2001", 3 pgs.
"U.S. Appl. No. 09/921,348, Response filed Mar. 30, 2005 to Non-Final Office Action mailed Jan. 26, 2005", 11 pgs.
"U.S. Appl. No. 09/921,348, Response filed Jul. 26, 2005 to Final Office Action mailed Jun. 27, 2005", 9 pgs.
"U.S. Appl. No. 09/921,348, Response filed Sep. 30, 2004 to Restriction Requirement mailed Sep. 20, 2004", 2 pgs.
"U.S. Appl. No. 09/921,348, Restriction Requirement mailed Sep. 20, 2004", 4 pgs.
"U.S. Appl. No. 10/291,200, Notice of Allowance mailed Nov. 10, 2005", 9 pgs.
"U.S. Appl. No. 10/291,200, Response filed Aug. 15, 2005 to Restriction Requirement mailed Jul. 18, 2005", 16 pgs.
"U.S. Appl. No. 10/291,200, Restriction Requirement mailed Jul. 18, 2005", 5 pgs.
"U.S. Appl. No. 11/038,996, Final Office Action mailed Feb. 4, 2008", 7 pgs.
"U.S. Appl. No. 11/038,996, Non-Final Office Action mailed Jul. 27, 2007", 4 pgs.
"U.S. Appl. No. 11/038,996, Notice of Allowance mailed May 21, 2008", 6 pgs.
"U.S. Appl. No. 11/038,996, Response filed Nov. 26, 2007 to Non Final Office Action mailed Jul. 27, 2007", 11 pgs.
"U.S. Appl. No. 11/038,996, Response filed Apr. 16, 2008 to Final Office Action mailed Feb. 4, 2008", 8 pgs.
"U.S. Appl. No. 11/151,567, Advisory Action mailed Dec. 4, 2008", 4 pgs.
"U.S. Appl. No. 11/151,567, Final Office Action mailed Apr. 6, 2010", 8 pgs.
"U.S. Appl. No. 11/151,567, Final Office Action mailed Sep. 5, 2008", 7 pgs.
"U.S. Appl. No. 11/151,567, Final Office Action mailed Dec. 28, 2009", 8 pgs.
"U.S. Appl. No. 11/151,567, Non-Final Office Action mailed Jan. 8, 2008", 11 pgs.
"U.S. Appl. No. 11/151,567, Non-Final Office Action mailed May 12, 2009", 7 pgs.
"U.S. Appl. No. 11/151,567, Non-Final Office Action mailed Oct. 15, 2010", 8 pgs.

"U.S. Appl. No. 11/151,567, Response filed Feb. 5, 2009 to Advisory Action mailed Dec. 4, 2008 and Final Office Action mailed Sep. 5, 2008", 18 pgs.
"U.S. Appl. No. 11/151,567, Response filed Mar. 1, 2010 to Final Office Action mailed Dec. 28, 2009", 19 pgs.
"U.S. Appl. No. 11/151,567, Response filed Apr. 8, 2008 to Non-Final Office Action mailed Jan. 8, 2008", 16 pgs.
"U.S. Appl. No. 11/151,567, Response filed Nov. 4, 2008 to Final Office Action mailed Sep. 5, 2008", 18 pgs.
"U.S. Appl. No. 11/151,567, Response filed Jun. 30, 2010 to Final Office Action mailed Apr. 6, 2010", 19 pgs.
"U.S. Appl. No. 11/151,567, Response filed Aug. 12, 2009 to Non Final Office Action mailed May 12, 2009", 17 pgs.
"U.S. Appl. No. 11/277,095, Non-Final Office Action mailed Aug. 4, 2008", 16 pgs.
"U.S. Appl. No. 11/277,095, Notice of Allowance mailed Jan. 21, 2009", 7 pgs.
"U.S. Appl. No. 11/277,095, Response filed Nov. 4, 2008 to Non Final Office Action mailed Aug. 4, 2008", 15 pgs.
"U.S. Appl. No. 11/287,631, Final Office Action mailed Aug. 21, 2008", 5 pgs.
"U.S. Appl. No. 11/287,631, Non-Final Office Action mailed Jan. 9, 2008", 5 pgs.
"U.S. Appl. No. 11/287,631, Non-Final Office Action mailed Jan. 27, 2009", 5 pgs.
"U.S. Appl. No. 11/287,631, Notice of Allowance mailed Sep. 10, 2009", 5 pgs.
"U.S. Appl. No. 11/287,631, Response filed Apr. 27, 2009 to Non Final Office Action mailed Jan. 27, 2009", 15 pgs.
"U.S. Appl. No. 11/287,631, Response filed May 8, 2008 to Non-Final Office Action mailed Jan. 9, 2008", 18 pgs.
"U.S. Appl. No. 11/287,631, Response filed Oct. 21, 2008 to Final Office Action mailed Aug. 21, 2008", 11 pgs.
"U.S. Appl. No. 12/206,198, Restriction Requirement mailed May 12, 2011", 6 pgs.
"U.S. Appl. No. 12/431,633, Non Final Office Action mailed Nov. 12, 2010", 12 pgs.
"U.S. Appl. No. 12/685,281, Non Final Office Action mailed Feb. 4, 2011", 5 pgs.
"U.S. Appl. No. 12/685,281, Notice of Allowance mailed May 13, 2011", 5 pgs.
"U.S. Appl. No. 12/685,281, Response filed Apr. 27, 2011 to Non Final Office Action mailed Feb. 4, 2011", 6 pgs.
"U.S. Appl. No. 12/685,281, Response filed Nov. 29, 2010 to Restriction Requirement mailed Oct. 28, 2010", 8 pgs.
"U.S. Appl. No. 12/685,281, Restriction Requirement mailed Oct. 28, 2010", 6 pgs.
"International Application Serial No. PCT/US00/06372, International Preliminary Examination Report mailed Jun. 13, 2001", 5 pgs.
"International Application Serial No. PCT/US00/06372, International Search Report mailed Jul. 7, 2000", 4 pgs.
"International Application Serial No. PCT/US00/06372, Written Opinion mailed Dec. 12, 2000", 5 pgs.
Cazares, Shelley, et al., "Arrhythmia Discrimination Based on Determination of Rate Dependency", U.S. Appl. No. 11/312,280, filed Dec. 20, 2005, 41 pgs.
Duru, Firat, et al., "The Potential for Inappropriate Ventricular Tachycardia Confirmation Using the Intracardiac Electrogram (EGM) Width Criterion", PACE, vol. 22, 1999, (Jul. 1999), 1039-1046.
Ellenbogen, Kenneth A, "Cardiac Pacing", Cambridge, Mass., USA : Blackwell Science, 2nd ed., (1996), 311-312 & 435-437.
Grady, T. A., et al., "Prognostic Significance of Exercise-Induced Left Bundle-Branch Block", JAMA, 279(2), (1998), 153-156.
Horowitz, L. N., et al., "Epicardial and Endocardial Activation During Sustained Ventricular Tachycardia in Man", Circulation, 61(6), (1980), 1227-1238.
Kinoshita, S., et al., "Transient Disappearance of Complete Right Bundle Branch (BBB) During Exercise", Journal of Electrocardiology, 29(3), (1996), 255-256.
Morris, Milton M, "Detection of Atrial Arrhythmia for Cardiac Rhythm Management by Implantable Devices", Journal of Electrocardiology, vol. 33, (2000), 133-139.

Ng, S. S., "Microcomputer-Based Telemetry System for ECG Monitoring", IEEE Proc. of the Ann. Int'l Conf. of the Engineering in Medicine and Biology Society, vol. Conf. 9, XP000015425, (1987), 1492-193.

SYSTEM FOR VERIFYING THE INTEGRITY OF CARDIAC COMPLEX TEMPLATES

CROSS REFERENCE TO RELATED APPLICATIONS

This application is a division of U.S. patent Ser. No. 12/685,281, filed Jan. 11, 2012, now issued as U.S. Pat. No. 8,019,408, which is a continuation of U.S. patent Ser. No. 11/287,631, filed on Nov. 28, 2005, now issued as U.S. Pat. No. 7,653,430, which is a divisional of U.S. patent Ser. No. 09/921,348, filed on Aug. 2, 2001, now issued as U.S. Pat. No. 6,996,434, which is a continuation of U.S. patent application Ser. No. 09/267,306, filed on Mar. 12, 1999, now issued as U.S. Pat. No. 6,312,388, the specifications of which are incorporated herein by reference.

FIELD OF THE INVENTION

This invention relates generally to medical devices, and more particularly to a system and method for verifying the integrity of normal sinus rhythm templates.

BACKGROUND

The heart is divided into four chambers, the left and right atrial chambers and the left and right ventricular chambers. As the heart beats, the atrial chambers and the ventricular chambers go through a cardiac cycle. The cardiac cycle consists of one complete sequence of contraction and relaxation of the chambers of the heart. The terms systole and diastole are used to describe the contraction and relaxation phases the chambers of the heart experience during a cardiac cycle. In systole, the ventricular muscle cells contract to pump blood through the circulatory system. During diastole, the ventricular muscle cells relax, causing blood from the atrial chamber to fill the ventricular chamber. After the period of diastolic filling, the systolic phase of a new cardiac cycle is initiated.

Through the cardiac cycle, the heart pumps blood through the circulatory system. Effective pumping of the heart depends upon five basic requirements. First, the contractions of cardiac muscle must occur at regular intervals and be synchronized. Second, the valves separating the chambers of the heart must fully open as blood passes through the chambers. Third, the valves must not leak. Fourth, the contraction of the cardiac muscle must be forceful. Fifth, the ventricles must fill adequately during diastole.

When the contractions of the heart are not occurring at regular intervals or are unsynchronized the heart is said to be arrhythmic. During an arrhythmia; the heart's ability to effectively and efficiently pump blood is compromised. Many different types of arrhythmias have been identified. Arrhythmias can occur in either the atrial chambers or in the ventricular chambers of the heart.

Ventricular tachycardia is an arrhythmia that occurs in the ventricular chambers of the heart. Ventricular tachycardias are typified by ventricular rates between 120-250 and are caused by disturbances (electrical or mechanical) within the ventricles of the heart. During a ventricular tachycardia, the diastolic filling time is reduced and the ventricular contractions are less synchronized and therefore less effective than normal. Ventricular tachycardias must be treated quickly in order to prevent the tachycardia from degrading into a life threatening ventricular fibrillation.

Arrhythmias that occur in the atrial chambers of the heart are referred to generally as supraventricular tachycardias. Supraventricular tachycardias include atrial tachycardias, atrial flutter and atrial fibrillation. During certain supraventricular tachycardias, aberrant cardiac signals from the atria drive the ventricles at a very rapid rate. Such a situation occurs during paroxysmal atrial tachycardia. This condition begins abruptly, lasts for a few minutes to a few hours, and then, just as abruptly, disappears and the heart rate reverts back to normal.

Cardioverter-defibrillators, such as implantable cardioverter-defibrillators (ICDs), have been shown to be effective in reducing the incidence of sudden cardiac death. Sudden cardiac death is typically caused by either ventricular tachycardia or ventricular fibrillation. Cardioverter-defibrillator systems operate by sensing and analyzing cardiac signals and applying electrical energy to the heart when either a ventricular tachycardia or ventricular fibrillation is detected.

One common way cardioverter-defibrillators detect cardiac arrhythmias is to sense and analyze the rate of ventricular contractions. When the ventricular rate exceeds a programmed threshold value, the cardioverter-defibrillator applies electrical energy in one or more specific patterns to treat either the ventricular tachycardia or ventricular fibrillation.

An additional method cardioverter-defibrillators use to detect cardiac arrhythmias is to compare the morphology of sensed cardiac complexes to template cardiac complexes representative of specific cardiac rhythms. As each cardiac complex is sensed, it is compared to the template cardiac complexes in an effort to identify and classify the sensed cardiac complex. Template cardiac complexes can be representative of a variety of cardiac complexes, including ventricular tachycardias and normal sinus rhythm.

Template cardiac complexes are typically programmed into an implantable medical device shortly before or after the device has been implanted into the patient. Once the implantable medical device has been implanted into the patient, however, the physiologic environment in which cardiac electrodes are placed (i.e., the heart) begins to change. These changes can include an inflammatory response, localized fibrosis around the implanted electrode and cardiac disease progression. These physiological changes lead to a deterioration, or a change in the strength and the morphology of the signal sensed by the implanted medical device. Additionally, changes in a patient's medication regimen can also change the sensing of cardiac signals by the implanted medical device. Therefore, cardiac complex templates developed before or soon after implanting the medical device can become less useful, or reliable, in the process of assessing and classifying unknown cardiac complexes.

Therefore, a need exists for addressing the changes in sensed cardiac signals as the physiological environment surrounding implanted cardiac electrodes changes.

SUMMARY OF THE INVENTION

The present subject matter provides a system and method to verify sensed normal sinus rhythm (NSR) cardiac complexes and to use the NSR cardiac complexes to update a NSR template. The system and method can either function automatically after a selected time interval has expired, or after commands have been delivered by a physician. As a result of updating, cardiac complexes being compared to the NSR template can be classified more accurately than if the cardiac complexes were compared to a NSR template that had not been updated.

Initially, a NSR template is created. In one embodiment, the NSR template is created by an implantable medical device, such as an implantable cardioverter defibrillator, under the control of a patient's attending physician. In creating a NSR template, cardiac complexes are sensed from a patient's heart. Values of one or more cardiac parameters are measured from each of the sensed cardiac complexes. In one embodiment, an implantable cardioverter defibrillator is used to sense cardiac complexes and to measure the values of the cardiac parameters. Cardiac parameters can include, but are not limited to, ventricular and atrial cycle lengths, widths of ventricular depolarizations, atrioventricular conduction times, and R-wave amplitudes.

The values of the cardiac parameters measured from the cardiac complexes are then compared to predetermined ranges for the values of the cardiac parameters for normal sinus rhythm (NSR) complexes. Based on this comparison, the cardiac complexes can be determined to be, or not to be, NSR cardiac complexes. When the cardiac complexes are determined to be NSR complexes, a NSR templates is calculated as a function of these NSR complexes.

After a selected time interval, the NSR template is examined to determine if it continues to accurately reflect the NSR cardiac complexes being sensed from the patient's heart. In one embodiment, values of cardiac parameters are measured from sensed cardiac complexes in a predetermined set of cardiac complexes. The values are then compared to predetermined value ranges. In one embodiment, the predetermined value ranges are individually established and programmed for each of the cardiac parameters. Values for each cardiac parameter measured are then compared to the corresponding predetermined value range established for that particular cardiac parameter.

When the values of the cardiac parameters are found to be within the predetermined value ranges, values for cardiac signal parameter differences are then calculated. The cardiac signal parameter difference values are calculated by taking the difference of the values of the cardiac parameters from each of the sensed cardiac complexes and the values of the cardiac parameters for the NSR template complexes. The values of the cardiac signal parameter differences are then compared to threshold values. In one embodiment, the threshold values for each of the cardiac signal parameter differences are calculated by multiplying a predetermined deviation percentage and each value of the cardiac parameters for the NSR cardiac complexes used to calculate the NSR template.

Based on the comparison, when the values for the cardiac signal parameter differences are found to be greater than the threshold values, the NSR template is updated as a function of the cardiac complexes. Alternatively, when the values for the cardiac signal parameter differences are found to be less than or equal to the threshold values, the NSR template is not updated.

DETAILED DESCRIPTION

Figure 1:
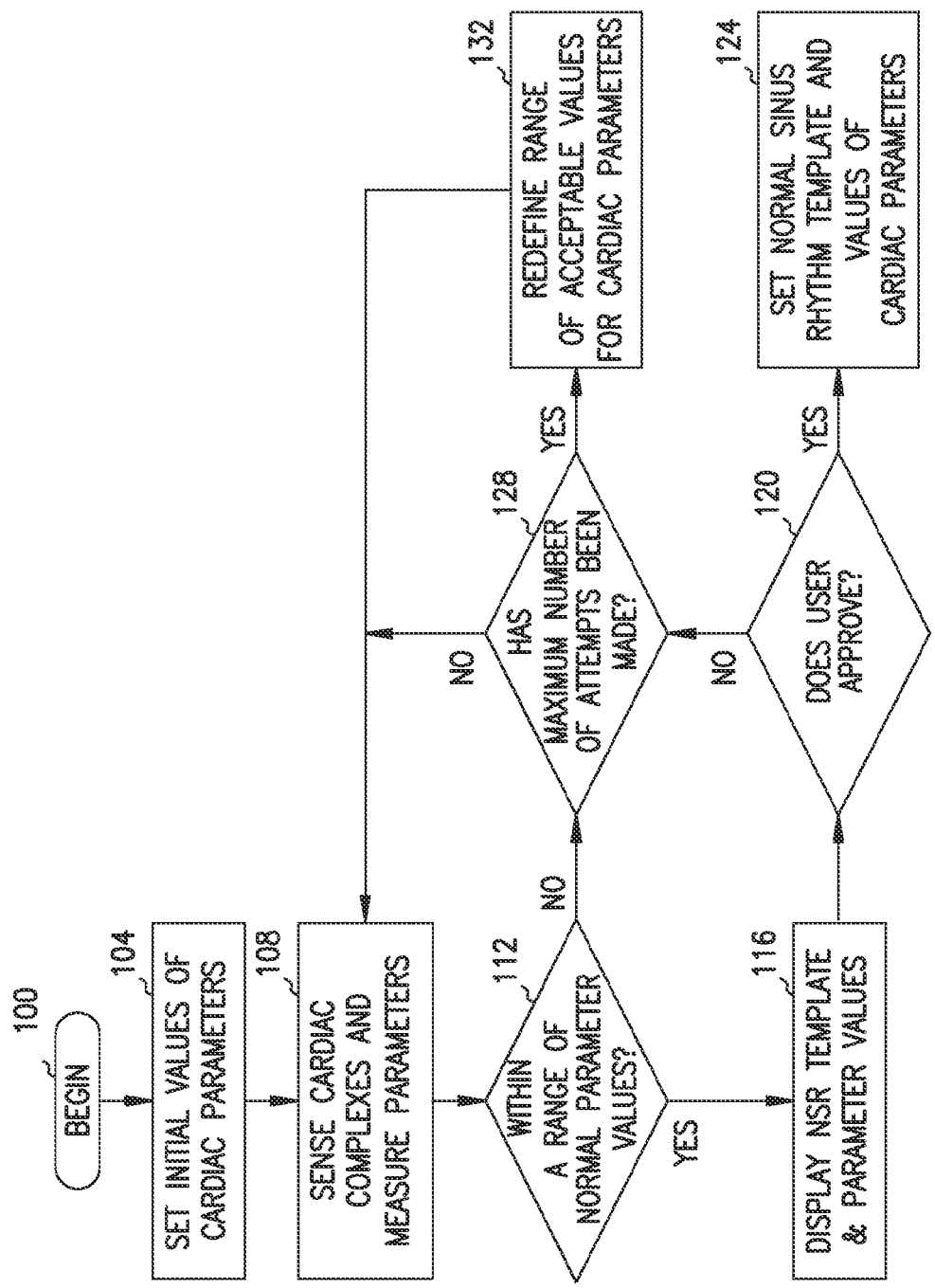
FIG. 1 is a flow chart illustrating one embodiment of the present subject matter.

In the following detailed description, reference is made to the accompanying drawings which form a part hereof and in which is shown by way of illustration specific embodiments in which the invention can be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims and their equivalents.

The embodiments illustrated herein are demonstrated in an implantable cardiac defibrillator (ICD), which may include numerous defibrillation, pacing, and pulse generating modes known in the art. However, these embodiments are illustrative of some of the applications of the present system, and are not intended in an exhaustive or exclusive sense. The concepts described herein can be used in a variety of applications which will be readily appreciated by those skilled in the art upon reading and understanding this description. For example, the present system is suitable for implementation in a variety of implantable and external devices.

The present subject matter allows for medical devices to examine and to recalculate or update a cardiac complex template. As previously discussed, medical device systems can use a cardiac complex template to assess and classify sensed cardiac complexes. Based on the classification of cardiac complexes, the medical device system can generate commands to cause the delivery of therapy to a patient's heart.

The physiologic environment in which cardiac electrodes are placed (i.e., the heart) changes from the moment the electrodes are implanted. Changes in the physiologic environment can include an inflammatory response and localized fibrosis around the implanted electrode due to the presence of the implanted electrode. These physiological changes, and other changes in cardiac disease, can lead to deterioration in sensing by the implanted medical device. Additionally, changes in a patient's medication regimen can also change the sensing of cardiac signals by the implanted medical device. Therefore, cardiac complex templates developed soon after implanting the medical device can become less reliable in the process of assessing and classifying unknown cardiac complexes.

The present subject matter allows for cardiac complex templates to be examined and, if certain predetermined conditions are met, to be recalculated. Recalculating cardiac complex templates can occur based on a determination that cardiac signals sensed during a cardiac state for which there is a cardiac complex template are no longer within a predetermined range of acceptability. In one embodiment, recalculation of the cardiac complex template is performed at specific time intervals over the life of the implantable medical device. Alternatively, the cardiac complex template is recalculated, or updated, at the direction of an attending physician when the physician determines the sensed cardiac signals have deviated sufficiently from the cardiac complex template signals.

In one embodiment, the present subject matter is useful for recalculating normal sinus rhythm (NSR) templates or models, such as the NSR template previously discussed. NSR templates are used in systems and methods where morphological features from cardiac signals sensed during a tachycardia event are compared to morphological features for cardiac signals sensed during normal sinus rhythm (e.g., the NSR templates). In one embodiment, procedures that compare values derived from NSR cardiac complexes are referred to as NSR template based procedures. In one embodiment, NSR template based procedures require that the NSR template be calculated, or derived at, from a patient's NSR cardiac complexes. However, as discussed above, as the cardiac tissue surrounding the cardiac leads change (e.g., as the tissue in which the lead is embedded changes) sensing of the cardiac complexes changes. Thus, there is a need for the NSR template to be updated after the medical device has been implanted.

Referring now to FIG. 1, there is shown an embodiment for creating a normal sinus rhythm (NSR) template. The procedure for setting the NSR template is started at 100. In one embodiment, the procedure for setting the NSR template is initiated by the patient's attending physician. Once the procedure is started at 100, values for one or more NSR parameters representative of the patient's normal sinus rhythm are set at 104. In one embodiment, the values of the NSR parameters are set by and programmed into the implantable medical device by the attending physician. In one embodiment, the values of the NSR parameters are based on a patient's previously recorded cardiac data and/or the patient's cardiac history. Alternatively, the values for the NSR parameters are a set of typical values for the NSR parameters.

In one embodiment, the values for the NSR parameters are derived from, but not limited to, the following cardiac parameters: ventricular cycle lengths (e.g., time between consecutively sense R-waves), atrial cycle lengths (e.g., time between consecutively sense P-waves), standard deviation of a plurality of ventricular cycle lengths, standard deviation of a plurality of atrial cycle lengths, width of ventricular depolarizations as manifested in the ventricular electrogram, atrioventricular conduction times, standard deviation of a plurality of atrioventricular conduction times, and standard deviation of a plurality of R-wave amplitudes as manifested in the ventricular electrogram. In one embodiment, the NSR parameters for which values are derived are selected and programmed into the medical device system through the use of a medical device programmer. In addition, the values for the NSR parameters are also programmed into the medical device system through the use of the medical device programmer.

After the values for the NSR parameters are set, these initial values must be checked against the values for the cardiac parameters measured from the patient's NSR cardiac complexes. At 108, one or more cardiac complexes are sensed from cardiac signals sensed from the patient's heart. In one embodiment, the cardiac signals are electrogram signals sensed through the use of the implanted medical device, such as an ICD, and include cardiac complexes representative of at least a portion of the cardiac cycle.

In one embodiment, the cardiac signals are viewed in real time on the display screen of the external medical device programmer. As the cardiac signal scrolls across the display screen, the user can select a series of cardiac complexes which he or she believes to be NSR complexes. The selected cardiac complexes are then tested against the initial values of the NSR parameters. This procedure saves valuable time by allowing only those cardiac complexes believed to be NSR complexes to be checked against the initial cardiac parameter values.

The implanted medical device measures and stores values for the one or more cardiac parameters from each of the sensed cardiac complexes. In one embodiment, the values for the one or more cardiac parameters are taken, or derived, from the cardiac parameters whose values were initially set at 104. At 112, the values of the one or more cardiac parameters are used to determine whether the sensed cardiac complexes are normal sinus rhythm (NSR) complexes. In one embodiment, the values of the one or more cardiac parameters are compared to values of the corresponding NSR parameters. In one embodiment, the values of the NSR parameters are those initially set at 104. In an alternative embodiment, the values of the NSR parameters are values of one or more cardiac parameters acquired during the process of setting the NSR template, an embodiment which will be described in greater detail below.

At 112, if the values of the cardiac signal parameters fall within a predetermined range of the values for the NSR parameters, then the NSR template and the values for the NSR parameters are displayed at 116. In one embodiment, displaying the NSR template and the values of the NSR parameters is done on the screen of the medical device programmer. Alternatively, the NSR template and the values of the NSR parameters are displayed on any suitably enabled display screen from which this information can be viewed.

The NSR template is calculated as a function of sensed NSR cardiac complexes. In one embodiment, after qualified NSR complexes have been identified, a single NSR complex can be formed to represent multiple NSR complexes. This is done by taking a sample by sample median, mean, or other statistic of one through n sensed NSR complexes, where n is an integer value representing the number of sensed NSR complexes. In one embodiment, n is an integer value in the range of 2 to 20 NSR complexes.

As the one through n NSR complexes are sensed, they are aligned around a common feature of the cardiac signal. In one embodiment, the common feature is a maximum deflection point of the cardiac signal as sensed during the occurrence of the ventricular R-wave. Other common features of the cardiac complexes can also be used to align the sensed NSR complexes. Once the NSR complexes have been aligned, median or mean values of the cardiac complexes are used to calculate the NSR template. Once the NSR template has been created from the sample by sample process, values for the NSR features are extracted from the NSR template and stored for use with the present subject matter. In an alternative embodiment, values for NSR features are measured for each of the sensed one through n NSR complexes. Median or mean values for the NSR feature values are calculated and the median or mean values are used to calculate the NSR template.

Once the NSR template and the values for the NSR parameter have been displayed, the attending physician can review the information. At 120, the physician can either approve of or not approve of the NSR template and the values for the NSR parameters proposed for use in the medical device. If the NSR template and the values for the NSR parameters are approved at 120, the NSR template and the values for the NSR parameters are programmed into the medical device system at 124 for subsequent use in discrimination procedures which rely on NSR templates and values of NSR parameters to distinguish one arrhythmic event from another.

If, however, the values of the cardiac signal parameters do not fall within values of the NSR parameters at 112 or the user does not approve of the NSR template and/or the values of the NSR parameters at 120, the system proceeds to 128. At 128, the number of attempts at setting the NSR template is determined. In one embodiment, when 128 is reached a value of one is added to the value of an attempt counter. In one embodiment, a predetermined threshold value is programmed for the attempt counter. In one embodiment, the predetermined threshold value is an integer value programmed in a range of 1 to 10, where 5 is an appropriate number.

When the number of attempts at setting the NSR template exceed the predetermined threshold value of the attempt counter, the range of acceptable values of the NSR parameters are redefined at 132. In one embodiment, redefining the values of the NSR parameters is done by the attending physician at the prompting the medical device programmer. Once redefined values for the NSR parameters are programmed, additional cardiac complexes are obtained at 108 and processed as previously described. Alternatively, if the number of attempts at setting the NSR template has not exceeded the predetermined threshold value of the attempt counter, the values of the NSR parameters are not redefined and additional cardiac complexes are obtained at 108 and processed as previously described.

Once a NSR template has been accepted and programmed into the implantable medical device, it can be used in the medical device system to assess and classify cardiac complexes. However, as the cardiac environment changes due to the presence of the cardiac lead (e.g., as cardiac tissue surrounding the implanted cardiac lead changes) so do the sensed cardiac signals. Changes in sensed cardiac signals necessitate updating the NSR template so that recently sensed cardiac complexes are analyzed with a NSR template that was also recently updated.

Figure 2:
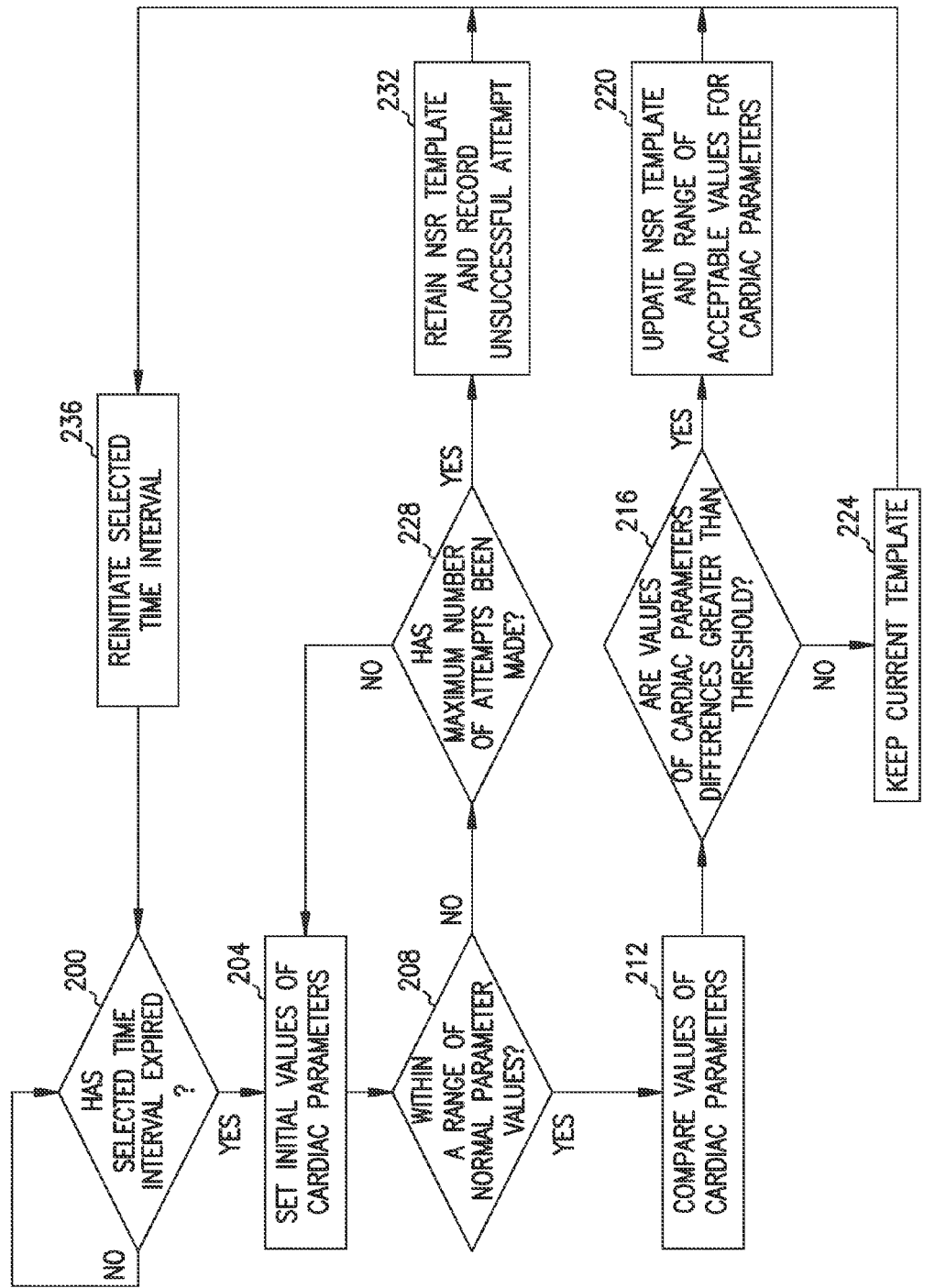
FIG. 2 is a flow chart illustrating one embodiment of the present subject matter.

In order to determine if the NSR template needs to be updated, it must first be examined and analyzed with respect to NSR cardiac complexes being sensed by the implantable medical device. Referring now to FIG. 2, there is shown one embodiment for examining a NSR template. In one embodiment, the NSR template is examined at a selected time interval after calculating the NSR template. Alternatively, the NSR template is examined at one or more selected time intervals (or times) after determining the NSR template.

At 200, the system determines if the selected time interval has elapsed. In one embodiment, the selected time interval is a programmable value in the range of 1 to 120 days, where 30 days is an appropriate length of time. In an alternative embodiment, the selected time interval can be programmed to become progressively shorter or longer after the medical device has been implanted in the patient. In one embodiment, the medical device system can update the NSR template more frequently early in life of the implantable medical device and become less frequent after a predetermined length of time. For example, the system can use two or more selected time intervals, where a first set of selected time intervals are used to trigger updates sooner than a second set of selected time intervals. In one embodiment, the first set of selected time intervals are used at an early stage after the implant of the medical device. The early stage after a medical device implant is when the physiological changes in the heart caused by the medical device's implant can alter the cardiac signals sensed by the medical device. Because of the degree of change in the sensed signals at this early stage of implant, the medical device may need to update the NSR template more often than when the medical device begins to receive more stable signals at a later date. In one embodiment, the early stages of a medical device implant can be considered to be between 0 and 3 months.

Alternatively, the time and/or date for updating the NSR template can be selected by the physician. In this way, the physician can program an update regimen most appropriate for the type of medical device being implanted into the patient and/or for the type of condition that the medical device will be most likely encounter. Alternatively, the physician can use the medical device programmer to send a signal to the implanted medical device to begin updating the NSR template.

At 200, the elapsed time is checked against the selected time interval to determine if the NSR template is to be updated. When the selected time interval expires, a predetermined set of cardiac complexes are analyzed for the purpose of examining the NSR template. In one embodiment, the cardiac signals are electrogram signals which contain cardiac complexes, or portions of cardiac complexes (e.g., P-waves, QRS-complexes, R-waves, etc.) sensed through the use of a medical device as previously discussed. As the predetermined set of cardiac complexes are sensed at 204, values for the one or more cardiac parameters are measured from each of the sensed cardiac complexes. At 204, the cardiac parameters measured from the sensed cardiac complexes include the cardiac parameters measured to determine the values of the NSR parameters. In one embodiment, the predetermined set of cardiac complexes is a programmable number of cardiac complexes in the range of 5 to 100, 5 to 50 or 5 to 20 cardiac complexes, where 10 cardiac complexes is an appropriate number.

The values of the one or more cardiac parameters measured at 204 are then compared to one or more predetermined value ranges for the cardiac parameters at 208. In one embodiment, the values of the one or more cardiac parameters are compared to the corresponding one or more predetermined value ranges (e.g., values ventricular intervals are compared to a predetermined value range for ventricular intervals, values for atrial intervals are compared to a predetermined value range for atrial intervals, etc.) In one embodiment, the predetermined value ranges used in 208 are value ranges for the cardiac parameters programmed by the patient's attending physician. In an alternative embodiment, the predetermined value ranges are the values of the cardiac parameters which were used to examine and subsequently update the NSR template through the present subject matter shown in FIG. 2.

In one embodiment, the predetermined value ranges represent values for cardiac parameters that are characteristic, or representative, of the patient's normal sinus rhythm. A major goal in examining and updating the NSR template is to ensure that the values of the cardiac parameters used to examine the NSR are from the patient's NSR cardiac complexes. The present system allows for verification that the NSR template update is accomplished with, or based on, cardiac complexes sensed during a patient's NSR and not inadvertently based on cardiac complexes sensed during a ventricular tachycardia, an atrial fibrillation, a sinus tachycardia or any other non-normal sinus rhythm cardiac condition.

At 208, when the values for the one or more cardiac parameters measured from the sensed cardiac signals are within the one or more predetermined value ranges, the system proceeds to 212. At 212, the values of the cardiac parameters from the sensed cardiac signals are compared with the values of cardiac parameters for the NSR complexes used to calculate the NSR template that is now being examined.

In one embodiment, comparing these values is accomplished by first taking differences between the values of the cardiac parameters from each of the sensed cardiac signals and the values of the cardiac parameters for the NSR complexes to give cardiac signal parameter differences. The values of the cardiac signal parameter differences are then compared to one or more threshold values. In one embodiment, the threshold values are percentage deviations from the values of the cardiac parameter for the NSR complexes. The predetermined percentage deviations can be programmed into the medical device, where the exact percentage deviation for each cardiac parameter will be programmed by the physician to a value that is most appropriate for that cardiac parameter. Additionally, percent deviations can also be augmented or replaced by a check to see if the cardiac parameters are within a predetermined range.

After comparing the values of the cardiac parameters at 212, the values of the cardiac signal parameter differences are compared to the threshold values at 216 to determine whether the values of the cardiac signal parameter differences are less than the threshold values. When the values of the cardiac signal parameter differences are greater than the threshold values, the values of the NSR parameters are replaced with the values of the one or more cardiac parameters from the predetermined set of cardiac complexes. The NSR template is then recalculated at 220 as a function of the cardiac complexes of the predetermined set of cardiac complexes. The medical device then records the updated NSR template and the updated values of the NSR parameters for use at 212 in a subsequent examination of the NSR template.

Alternatively, if at 216, the values of the cardiac signal parameter differences are less than or equal to the threshold values, the values of the NSR parameters and the NSR template currently being examined are retained at 224 (i.e, not replaced). After either 220 or 224, the timer for updating the template is reinitiated at 236. Once the timer for updating has been reinitiated, the elapsed time is again checked against the selected time interval at 200 to determine if the NSR template is to be updated.

Referring again to 208, if the values of the cardiac parameters measured from the sensed cardiac signals are not within the predetermined value range, the system proceeds to 228. At 228, the number of times the values of the cardiac parameters have been tested against the predetermined value range system is determined. In one embodiment, when 228 is reached, a value of one (1) is added to an attempt counter value. In one embodiment, the attempt counter value has initial value of zero at the start of the NSR template updating process.

After the one has been added to the value of the attempt counter, the new value of the attempt counter is compared to a predetermined threshold value at 228. In one embodiment, the predetermined threshold value is a programmable value of the number of attempts to be made at determining whether the cardiac parameter values measured from the sensed cardiac signals are within the predetermined value range at 208. In one embodiment, the predetermined threshold value is an integer value programmed in a range of 1 to 10, where 5 is an appropriate number.

When the number of attempts at updating the NSR template and the values of the cardiac parameters exceeds the value of the attempt counter, the NSR template and the values of the cardiac parameters are retained (i.e., not changed) and the attempt to update the NSR template and the cardiac signal parameter is recorded in the medical device system at 232. In one embodiment, a record of all successful and unsuccessful NSR template updates is stored and can be displayed at follow-up visits for diagnostic purposes.

After recording the attempt at updating the NSR template, the timer for updating the template is reinitiated at 236. Once the timer for updating has been reinitiated, the elapsed time is again checked against the selected time interval at 200 to determine if the NSR template is to be updated. In addition to reinitiating the update timer, the attempt number for 228 is reset to zero.

Alternatively, when the number of attempts at updating the NSR template and the values of the cardiac parameters do not exceed the value of the attempt counter, additional cardiac parameters are measured from sensed cardiac complexes at 204. The cardiac parameter values determined at 204 are then compared to the predetermined value ranges for the cardiac parameters as previously described.

The present subject matter is useful with any number of external or implantable medical device systems which use NSR templates in analyzing, or assessing, a patient's cardiac condition. In one embodiment, cardiac complexes are sensed and analyzed using an implantable medical device, where the implantable medical device includes a transvenous lead system to allow sensing of the cardiac action potentials. The transvenous lead system can include a rate-sensing electrode and at least one defibrillation electrode positioned on the transvenous lead. Cardiac action potentials sensed using defibrillation electrodes are typically referred to as far-field signals (or morphology signals) and cardiac action potentials sensed using rate sensing, or pacing, electrodes are typically referred to as near-field signals (or rate signals).

In one embodiment, the rate-sensing electrode is a pacing tip electrode positioned at the distal end of the transvenous lead system. Other types of rate sensing electrodes are also considered appropriate to use with the present subject matter. Examples of other types of rate sensing electrodes include ring electrodes, both annular and semi-annular, as are known in the art. Rate sensing using the transvenous lead system can also be accomplished either through unipolar or bipolar sensing methods, as are known.

Figure 3:
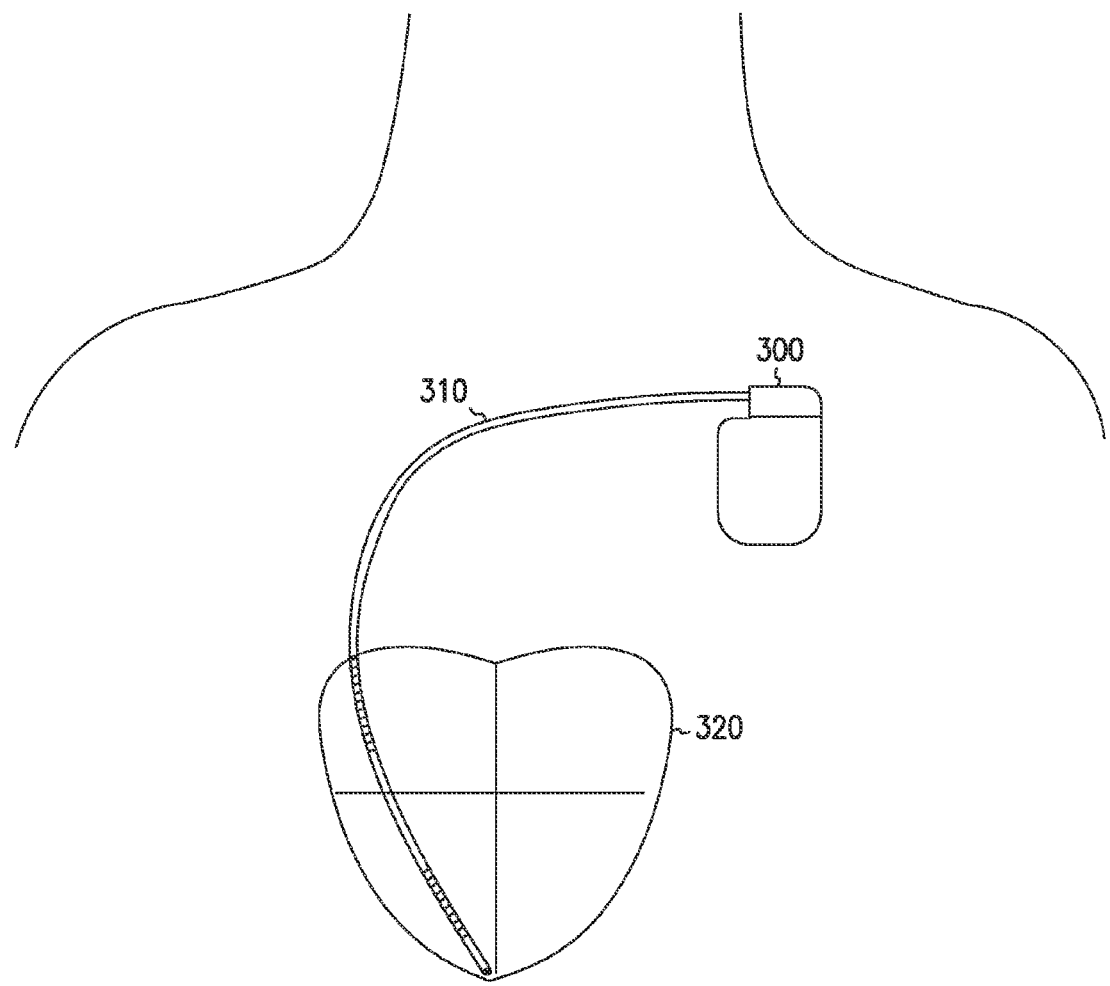
FIG. 3 is a schematic of an implantable medical device.

In one embodiment, the implantable medical device system can employs an single body lead catheter sold under the trademark ENDOTAK (Cardiac Pacemaker, Inc./Guidant Corporation, St. Paul, Minn.) having a pacing tip electrode and two defibrillation coil electrodes. One example of such a system is shown in FIG. 3. An implantable cardioverter defibrillator (ICD) 300 is coupled to catheter 310, which is implanted to receive signals from heart 320. The catheter 310 also may be used for transmission of pacing and/or defibrillation signals to the heart 320. In an alternative embodiment, a three defibrillation electrode system is employed, wherein the housing of the implantable system is used as a third defibrillation electrode.

In one example, the ICD 300 senses cardiac signals from the heart 320. When the ICD 300 detects the occurrence of an arrhythmic event, the ICD 300 analyzes the sensed arrhythmic complexes (i.e., the cardiac signals) of the arrhythmic event. In one embodiment, the ICD analyzes and compares the sensed arrhythmic complexes with respect to the NSR template to assess the origin of a cardiac arrhythmia (e.g., determining a ventricular tachycardia (VT) versus a supraventricular tachycardia (SVT). Based on the comparison, the ICD 300 is able to distinguish SVT events from VT events and, depending upon the ICD's classification of the arrhythmic event, to provide appropriate therapy to treat the heart 320. Some methods useful for distinguishing SVT events from VT events are presented in U.S. Pat. No. 6,223,078, entitled "Discrimination of Supraventricular Tachycardia and Ventricular Tachycardia Events", the specification of which is hereby incorporated by reference in its entirety.

Figure 4:
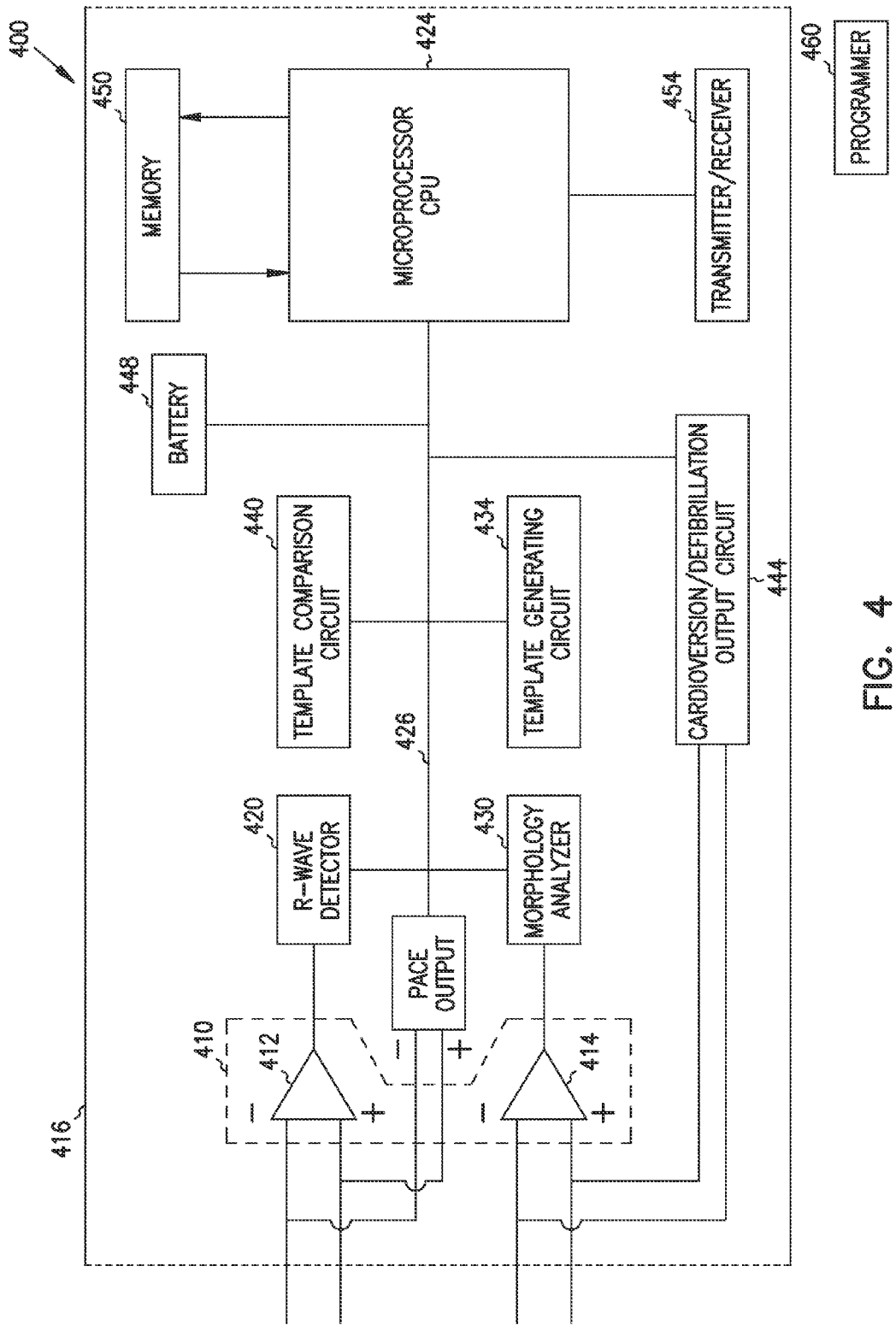
FIG. 4 is one embodiment of a block diagram of an implantable medical device according to the present subject matter.

Referring now to FIG. 4, there is shown one embodiment of an implantable cardiac defibrillator (ICD) 400, which may include numerous defibrillation, pacing, and pulse generating modes known in the art. An endocardial lead is physically and electrically coupled to the ICD 400. The endocardial lead can include at least one pacing electrode and at least one defibrillation coil electrode as are known. In one embodiment, the endocardial lead is an ENDOTAK lead as previously described.

FIG. 4 discloses ICD 400 which includes input circuitry 410. In one embodiment, input circuitry 410 includes a first amp 412 and a second amp 414. The first amp 412 receives rate-signals or near-field signals through the at least one pacing electrode. In one embodiment, the rate-signals are sensed using a unipolar configuration, where the cardiac signals are sensed between the at least one pacing electrode and the housing 416 of the ICD 400. Alternatively, bipolar sensing is accomplished between two or more pacing electrodes on one or more endocardial leads. The second amp 414 receives morphology-signals, or far-field signals, from at least two defibrillation coil electrodes located on the endocardial lead.

An R-wave detector circuit 420 receives the rate-signals from the first amp 412. The R-wave detector circuit 420 detects R-waves from the rate-signals being received by the first amp 412 and conveys information relating to the cardiac rate to a microprocessor 424 by a data bus 426. A morphology analyzer circuit 430 receives morphology signals from the second amp 414. In one embodiment, the morphology analyzer circuit 430 extracts and measures the values of the cardiac parameters from the sensed cardiac complexes. A template generating circuit 434 is coupled to the signal morphology analyzing circuit 430 by the bus 426. The template generating circuit 434 receives the values of the cardiac parameters. In one embodiment, the template generating circuit 434 calculates, or updates, the NSR template as a function of the sensed NSR cardiac complexes.

A template comparison circuit 440 is coupled to the template circuit 434 by bus 426. In one embodiment, the template comparison circuit 440 compares the values of the cardiac parameters to the predetermined value ranges for the cardiac parameters. When the values of the cardiac parameters are within the predetermined value ranges the template comparison circuit 440 compares the values of the cardiac parameters from the sensed cardiac signals with the values for the cardiac parameters of the NSR cardiac complexes used to determine the NSR template. As previously discussed, the cardiac signal parameter differences between the values of the cardiac parameters and the values of the cardiac parameters used to determine the NSR template are compared to corresponding threshold values. In one embodiment, the template comparison circuit 440 calculates the threshold values by multiplying a predetermined deviation percentage and the values of the cardiac parameters for the NSR cardiac complexes used to calculate the NSR template.

After comparing the cardiac signal parameters, the template comparison circuit 440 compares the values of the cardiac signal parameters differences to the threshold values to determine whether the values of the cardiac signal parameter differences are less than the threshold values. When the values of the cardiac signal parameter differences are greater than the threshold values, the template generating circuit 434 recalculated, or update, the NSR template as a function of the sensed cardiac complexes. In an additional embodiment, the template comparison circuit 440 determines the number of times the values of the cardiac parameters have been tested against the predetermined value range system, and increases the value of the attempt counter during each attempt to update the NSR template.

Power to operate the ICD 400 is supplied by a battery 448. Memory 450 is also provided in the ICD 400, and is connected with the microprocessor 424. In one embodiment, the values of the cardiac signal parameters used to redefine the NSR template are recorded in a memory circuit 450 of the ICD 400. Additionally, the attempts made to update the NSR template and the cardiac signal parameter are also stored in the memory 450 of the ICD 400. The ICD 400 further includes a transmitter receiver 454, which can be used to communicate with the microprocessor 424 through a programmer 460 as is known.

The embodiments provided herein are intended to demonstrate only some of the embodiments of the present system. Other embodiments utilizing the present subject matter are can be appreciated by those skilled in the art. For example, the concepts of the present subject matter are expressly described in terms of cardiac complexes sensed for the QRS-wave of the heart, however, applications to other cardiac complexes, including P-wave complexes or a combination of QRS-wave and P-wave complexes, can be readily appreciated by those skilled in the art without departing from the present invention.

Also, a dual chamber implantable cardiac defibrillator can be used to take advantage of the present subject matter. In one embodiment, the dual chamber implantable cardiac defibrillator includes an ENDOTAK single body lead catheter implanted in the ventricular region of the heart and an atrial catheter implanted in a supraventricular region of the heart. This embodiment allows for ventricular near-field signals and ventricular far-field signals, along with atrial near-field signals to be sensed and analyzed by the implantable cardiac defibrillator.

Other cardiac defibrillator systems and catheter configurations may also be used without departing from the present system. In addition to ICD systems, the present system may be utilized in external defibrillation systems and in external cardiac monitoring systems. In addition to employing endocardial leads, the present system can also utilize body surface leads.

Additionally, even though NSR templates were discussed herein, other templates, including templates for specific cardiac complexes and arrhythmic cardiac events, can also be recorded, analyzed, and up-dated using the inventive concepts embodied in the present subject matter, and therefore, the express teachings of this disclosure are not intended in an exclusive or limiting sense.

What is claimed is:

1. A device, comprising:
   a morphology analyzer adapted to extract and measure sensed cardiac complex parameter values;
   a template generating circuit connected to the morphology analyzer and adapted to receive the sensed cardiac complex parameter values and generate a cardiac complex template; and
   a template comparison circuit connected to the template generating circuit and adapted to compare sensed cardiac complex parameter values to reference cardiac parameter values to determine if the sensed cardiac complex parameter values and the reference cardiac parameter values have a difference greater than a threshold,
   wherein the template comparison circuit and the template generating circuit cooperate to update the cardiac complex template upon determining that the difference is greater than the threshold.

2. The device of claim 1, wherein the cardiac complex template includes an arrhythmia template.

3. The device of claim 1, wherein the cardiac complex template includes a normal sinus template.

4. The device of claim 1, wherein the template comparison circuit and the template generating circuit cooperate to update the cardiac complex template after expiration of a programmed time interval.

5. The device of claim 1, wherein the template comparison circuit and the template generating circuit cooperate to update the cardiac complex template after expiration of a programmed time interval and to update the cardiac complex template after expiration of another programmed time interval.

6. The device of claim 1, wherein the device is configured to retain the cardiac complex template if the template comparison circuit determines that the sensed cardiac complex parameter values are acceptable.

7. The device of claim 1, wherein the template comparison circuit is configured to automatically compare sensed cardiac complex parameter values to reference cardiac parameter values after a programmed time period.

8. The device of claim 1, wherein the template comparison circuit is configured to compare sensed cardiac complex parameter values to reference cardiac parameter values in response to a physician-initiated command.

9. The device of claim 1, wherein the reference cardiac parameter values include physician-programmed values.

10. The device of claim 1, wherein the template comparison circuit and the template generating circuit cooperate to create an initial cardiac complex template using one or more sensed cardiac complex values if the one or more sensed cardiac complex parameter values are acceptable.

11. The device of claim 10, wherein the device is configured to redefine acceptable cardiac complex parameter values after a number of attempts have been made to create the initial cardiac complex template.

12. The device of claim 1, wherein the reference cardiac parameter values are typical cardiac complex parameter values.

13. The device of claim 1, wherein the reference cardiac parameter values are specific to a patient's cardiac history.

14. The device of claim 1, wherein the device is an implantable cardioverter defibrillator.

15. A device, comprising:
input circuitry configured to be electrically connected to at least one electrode to sense cardiac complexes;
a morphology analyzer circuit connected to the input circuitry and configured to measure sensed cardiac complex parameter values;
a template generating circuit connected to the morphology analyzer circuit and configured to receive the sensed cardiac complex parameter values and generate a complex cardiac template;
a template comparison circuit connected to the template generating circuit and adapted to compare sensed cardiac complex parameter values to reference cardiac parameter values after a time interval has elapsed to determine if the sensed cardiac complex parameter values and the reference cardiac parameter values have a difference greater than a threshold; and
a microprocessor operably connected to the input circuitry, the morphology analyzer circuit, the template generating circuit, and the template comparison circuit, wherein the microprocessor includes a timer for determining the time interval,
wherein the template comparison circuit and the template generating circuit cooperate to update the cardiac complex template upon determining that the difference is greater than the threshold.

16. The device of claim 15, further comprising a display connected to the microprocessor.

17. The device of claim 15, further comprising a detector circuit operably connected to the input circuitry and configured to convey information relating to cardiac rate to the microprocessor.

18. The device of claim 15, further comprising a memory circuit operably connected to the microprocessor and configured to store the cardiac complex template and the reference cardiac parameter values.

19. The device of claim 15, wherein the template comparison circuit and the template generating circuit are configured to cooperate to update the cardiac complex template when the sensed cardiac complex parameter values vary from a current cardiac complex template by a threshold value.

20. The device of claim 19, wherein the threshold value is a predetermined deviation percentage of parameter values for the current cardiac complex.

21. The device of claim 15, wherein the time interval is programmable.

22. The device of claim 21, wherein the device is an implantable device, and the time interval is programmable to be progressively longer after the device has been implanted in a patient.

* * * * *